United States Patent
Lee (10) Patent No.: US 10,199,025 B2
(45) Date of Patent: Feb. 5, 2019

(54) IMAGE CAPTURING DEVICE AND ELECTRONIC KEYBOARD USING THE IMAGE CAPTURING DEVICE

(71) Applicant: Moon Key Lee, Seoul (KR)

(72) Inventor: Moon Key Lee, Seoul (KR)

(*) Notice: Subject to any disclaimer, the term of this patent is extended or adjusted under 35 U.S.C. 154(b) by 0 days.

(21) Appl. No.: 15/505,723

(22) PCT Filed: Aug. 22, 2015

(86) PCT No.: PCT/KR2015/008789
§ 371 (c)(1),
(2) Date: Feb. 22, 2017

(87) PCT Pub. No.: WO2016/032176
PCT Pub. Date: Mar. 3, 2016

(65) Prior Publication Data
US 2017/0278499 A1    Sep. 28, 2017

(30) Foreign Application Priority Data

Aug. 23, 2014   (KR) .................. 10-2014-0110154
Jan. 24, 2015   (KR) .................. 10-2015-0011636

(51) Int. Cl.
*G10H 1/34*   (2006.01)
*G01N 21/41*  (2006.01)
(Continued)

(52) U.S. Cl.
CPC ............. *G10H 1/34* (2013.01); *G01N 21/41* (2013.01); *G02B 5/045* (2013.01); *G02B 5/12* (2013.01);
(Continued)

(58) Field of Classification Search
CPC . G10H 1/34; G01N 21/41; G02B 5/12; G06K 9/209; G06K 9/78; G10C 3/12
(Continued)

(56) References Cited

U.S. PATENT DOCUMENTS 2,168,886 A * 8/1939 Roberts .................. B41J 3/44
                                                 235/145 R
3,886,544 A * 5/1975 Narodny ............. G02B 6/3574
                                                 250/227.22
(Continued)

FOREIGN PATENT DOCUMENTS

JP   10-2002-0069712 A   9/2002
JP       2004-198761 A   7/2004
(Continued)

OTHER PUBLICATIONS

Translation of KR 20060077382A.*

*Primary Examiner* — Elvin G Enad
*Assistant Examiner* — Christina Schreiber
(74) *Attorney, Agent, or Firm* — Leydig Voit and Mayer (57) ABSTRACT

An electronic keyboard using a camera, and more particularly, to an electronic keyboard using a camera, which includes a retroreflective film, a light source for irradiating light on to the retroreflective film, a camera for capturing light of a light source retroreflected from the retroreflective film, and an image processing means that analyzes the captured image to track the position of the reflected light source, to find a depressed state of the keyboard, and to generate a sound of an instrument corresponding to the depressed state.

9 Claims, 12 Drawing Sheets

(51) Int. Cl.
| | |
|---|---|
| *G02B 5/12* | (2006.01) |
| *G06K 9/20* | (2006.01) |
| *G06K 9/78* | (2006.01) |
| *G10C 3/12* | (2006.01) |
| *G02B 5/04* | (2006.01) |
| *G02B 26/08* | (2006.01) |
| *G06K 9/00* | (2006.01) |
| *G06K 9/46* | (2006.01) |
| *G10H 1/055* | (2006.01) |

(52) U.S. Cl.
CPC ........... *G02B 26/0816* (2013.01); *G06K 9/00* (2013.01); *G06K 9/209* (2013.01); *G06K 9/2018* (2013.01); *G06K 9/2063* (2013.01); *G06K 9/4652* (2013.01); *G06K 9/78* (2013.01); *G10C 3/12* (2013.01); *G10H 1/0553* (2013.01); *G10H 1/344* (2013.01); *G10H 2220/305* (2013.01); *G10H 2220/455* (2013.01)

(58) Field of Classification Search
USPC .......................................................... 84/744
See application file for complete search history.

(56) References Cited

U.S. PATENT DOCUMENTS

| | | | | |
|---|---|---|---|---|
| 4,113,353 A * | 9/1978 | Matsushita | ............. | G06F 3/042 250/227.31 |
| 4,379,968 A * | 4/1983 | Ely | ...................... | H03K 17/969 250/229 |
| 4,641,026 A * | 2/1987 | Garcia, Jr. | ............. | G06F 3/0202 250/229 |
| 4,868,568 A * | 9/1989 | Souloumiac | ......... | H03K 17/969 341/31 |
| 5,909,028 A * | 6/1999 | Yamamoto | ............... | G01D 5/34 250/221 |
| 5,910,348 A | 6/1999 | Hart-Smith et al. | | |
| 7,446,677 B2 * | 11/2008 | Wald | .................... | G06F 3/0202 250/229 |
| 7,924,175 B2 * | 4/2011 | Gitzinger | .............. | G06F 3/0202 241/22 |
| 8,022,942 B2 * | 9/2011 | Bathiche | ............... | G06F 3/0238 345/173 |
| 9,367,204 B2 * | 6/2016 | Xue | .................... | G06F 3/04815 |
| 9,477,310 B2 * | 10/2016 | Cherradi El Fadili | ...................... | G06F 3/017 |
| 9,557,846 B2 * | 1/2017 | Baharav | ................ | G06F 3/0421 |
| 9,626,043 B2 * | 4/2017 | Yang | ..................... | G06F 3/0428 |
| 9,797,752 B1 * | 10/2017 | Ruh | ...................... | G01D 5/3473 |
| 9,846,492 B2 * | 12/2017 | Chen | .................... | H03K 17/969 |
| 9,857,892 B2 * | 1/2018 | Armstrong-Muntner | ...................... | G06F 3/042 |
| 2002/0021287 A1 * | 2/2002 | Tomasi | ................. | G06F 1/1613 345/168 |
| 2005/0139060 A1 * | 6/2005 | Muramatsu | .......... | G10H 1/0553 84/719 |
| 2005/0237390 A1 * | 10/2005 | Mittal | .................... | G06K 9/209 348/169 |
| 2006/0024017 A1 * | 2/2006 | Page | ...................... | G02B 6/002 385/146 |
| 2008/0180654 A1 * | 7/2008 | Bathiche | ............... | G06F 3/0238 356/51 |
| 2010/0149099 A1 * | 6/2010 | Elias | ..................... | G06F 1/1616 345/168 |
| 2010/0283831 A1 * | 11/2010 | Takahashi | ............ | G02B 17/086 348/36 |
| 2011/0006991 A1 * | 1/2011 | Elias | ..................... | G06F 1/1662 345/168 |
| 2013/0011097 A1 * | 1/2013 | Jung | ..................... | G02B 6/4214 385/31 |
| 2014/0132516 A1 * | 5/2014 | Tsai | ...................... | G06F 3/0202 345/168 |
| 2016/0210950 A1 * | 7/2016 | McPherson | ......... | G06F 3/03547 |
| 2016/0306437 A1 * | 10/2016 | Zhang | .................. | G06F 1/1662 |
| 2017/0278499 A1 * | 9/2017 | Lee | ......................... | G10H 1/34 |

FOREIGN PATENT DOCUMENTS

| | | | |
|---|---|---|---|
| JP | 2007-528028 A | | 10/2007 |
| JP | 2008306350 A | * | 12/2008 |
| JP | 2010-183490 A | | 8/2010 |
| JP | 2010183490 A | * | 8/2010 |
| KR | 10-2004-0049045 A | | 6/2004 |
| KR | 10-2004-0065957 A | | 7/2004 |
| KR | 10-2006-007382 A | | 7/2006 |
| KR | 20060077382 A | * | 7/2006 |
| KR | 10-1007649 B1 | | 1/2011 |
| WO | WO 2005/085936 A1 | | 9/2005 |
| WO | WO 2005085936 A1 | * | 9/2005 | ............... G02B 5/04 |

* cited by examiner

IMAGE CAPTURING DEVICE AND ELECTRONIC KEYBOARD USING THE IMAGE CAPTURING DEVICE

TECHNICAL FIELD

The present invention relates to a row division optical module capable of observing a long object at a high resolution and an electronic keyboard.

BACKGROUND ART

The present invention relates to a row division optical module capable of capturing an image of a long object, such as a keyboard, at a high resolution, of more than one key at a time, and an electronic keyboard using the same.

DETAILED DESCRIPTION OF THE INVENTION

Technical Problem

To observe left and right long objects at a glance, such as keyboards having a large number of keys on a piano, an observer must be far enough away to see the entire object at a glance. When you are far away, you can see the entire object at a glance, but the object is small, making it difficult to observe the object in detail. The present invention has been made to solve the above-mentioned problems, and it is an object of the present invention to provide a row division optical module and an electronic keyboard using the same.

Technical Solution

The present invention provides a row division optical module, such as a prism, in which a left side (or right side) of a long object is visible above the visual field and a remaining right side (or left side) is visible below the visual field. By installing such an optical module in front of a lens of a camera, a long object can be captured over the entire area of the object at a high resolution. With such a camera, it is possible to capture an image of an object with a large number of keys to the far left and the far right of a piano at a high resolution at once, to detect movement of a key on a keyboard in an image captured by an image processing means, and to output a musical instrument sound or a midi signal.

Advantageous Effects

Conventional digital pianos are equipped with sensors or switches for detecting the movement of each key in the keyboard, so that it is difficult to manufacture due to a large number of parts and a complicated circuit, it is easy to break down and is heavy. However, a piano using the row division optical module and the camera according to the present invention can be easily manufactured and will improve the reliability of the electronic circuit by replacing a complicated switch circuit provided for each key with a simple and small camera, and a camera module that can be purchased and manufactured by assembling them directly, so that a digital piano can be realized at low cost.

Also, there is no printed circuit board (PCB) and sensor circuit under the keyboard, so it has the advantage of lightness of the keyboard, and the keyboard can be made of transparent material, which can be designed to look like a jewel and provide visual beauty.

BEST MODE

Embodiment 1

In the electronic piano, when a key is pressed, a switch connected to the key is pressed, and the scanning circuit detects the key and outputs a sound of a musical instrument corresponding to the key. Since such a device is provided with a switch for each key, it is difficult to manufacture due to a large number of components, easy to experience trouble, and includes complicated wiring. Complex circuits and wiring are not visually beautiful, so they are covered with opaque cases. These opaque cases are frustrating to look at. The present invention can eliminate such an opaque case by replacing such a complicated circuit with a compact and reliable camera to improve the key part simply and visually. It is also possible to make the keys transparent as a jewel to provide a beautiful feeling without being visually stifling. Also, by removing the printed circuit board of the switch circuit, it is easy to manufacture and reduce the generation of industrial waste.

The above piano with camera can be configured as following. A mark such as a retroreflective film (SR) is attached to a portion where each key (KE) moves greatly, and a light source (LS) such as an infrared LED and a camera (CM) are attached to each other and installed, and when the light emitted from the light source (LS) reaches the camera (CM) after being retroreflected by the retroreflective film (SR), the light is captured by the camera, the position of the retroreflective film is analyzed in order to detect the degree of depression of the key wherein the analyzing is processed by image processing means, and a sound corresponding to the degree of depression of the key can be generated.

In the case of using an infrared light source, it is preferable to attach a filter in front of the camera to allow only infrared rays reach the camera. This makes it easy to detect movement on the keyboard because the background is black and only the light retroreflected by the retroreflective film is brightly captured.

Instead of using a separate infrared LED, ambient light can be used, and a common mark can be used instead of a separate retroreflective film. If the difference image between the currently captured image and the previously captured image is obtained, It is easy to detect the motion of key because the difference pixel value becomes 0 in the background without key motion, and the pixel value of the mark portion on the moving key is not 0, wherein the difference image means that the pixel value of the difference image is the difference value between two pixels in the overlapping position of two overlapping images when the two images are overlapped.

Figure 1:
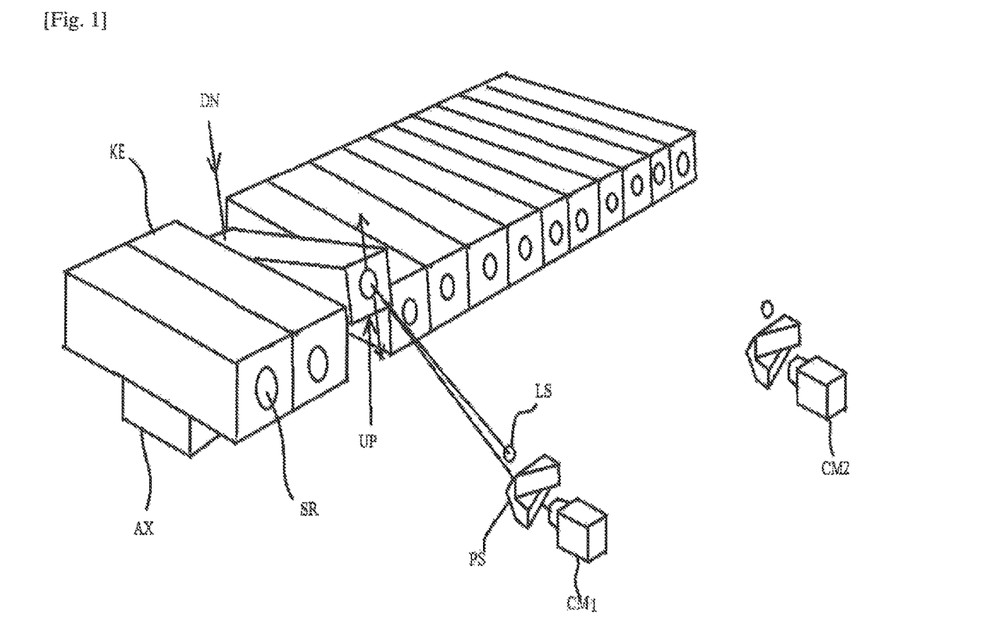
FIG. 1 is a block diagram of an embodiment of the present invention.

In FIG. 1, the keyboard is placed on the support bar (AX), and one end of the keyboard is pressed (DN) and the other end is raised (UP) about the support bar (AX). When the keyboard rotates like this, the position of the retroreflective film that is captured by the camera changes, and by analyzing the position, the degree of rotation of the key (that is, the degree to which the key is pressed) can be found.

Figure 11:
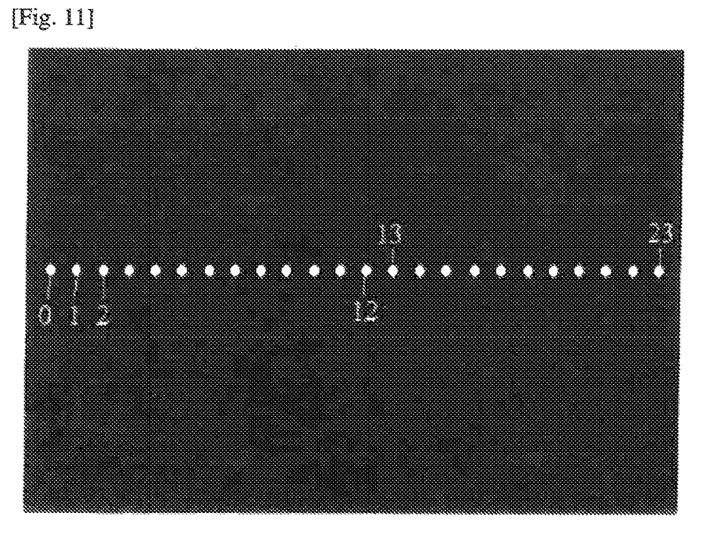
FIG. 11 is an image of marks of a keyboard captured without row division prism installed in front of a camera.

If there are a large number of keys, it may not be possible to capture all the keys by one camera. In order to capture all the keys by one camera, it is necessary to increase the distance between the camera and the keyboard. However, there is a problem that it is difficult to track the position of the keyboard because the retroreflective film is too small in captured image as shown in FIG. 11.

Figure 3:
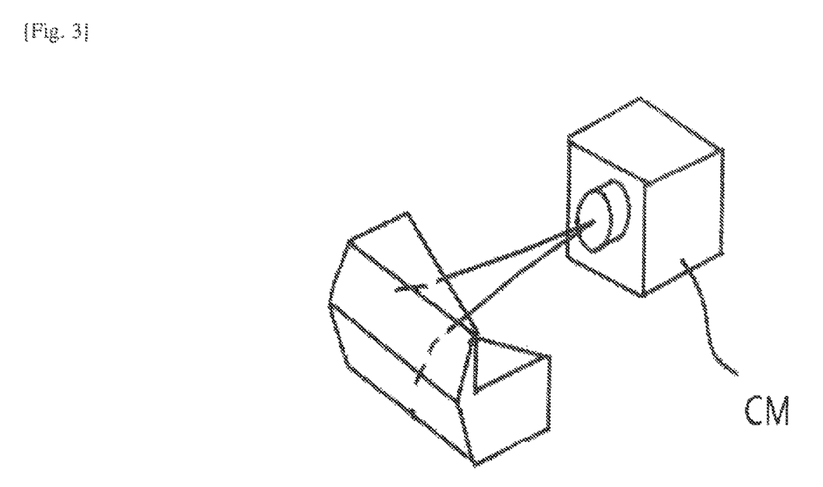
FIG. 3 is a perspective view of the row division prism.
Figure 4:
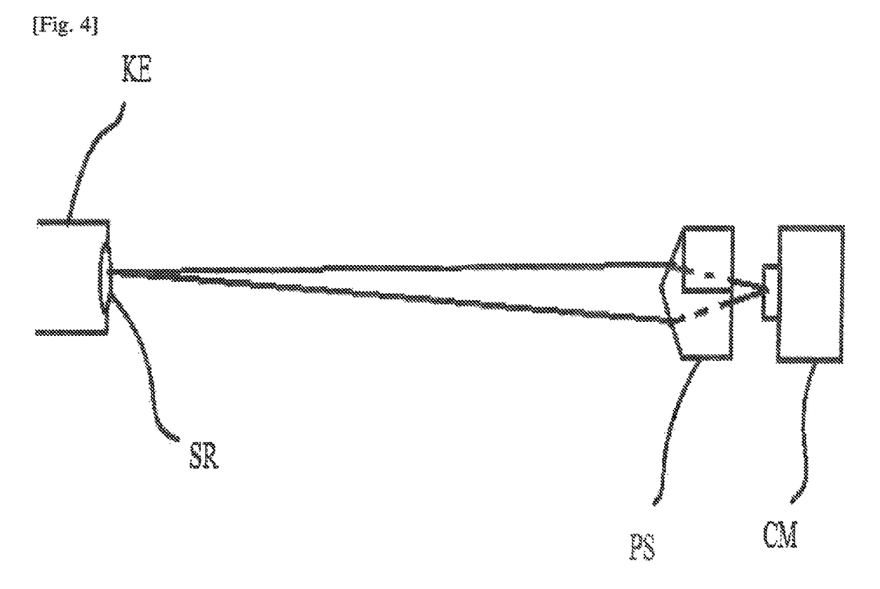
FIG. 4 is a side view of the row division prism.
Figure 5:
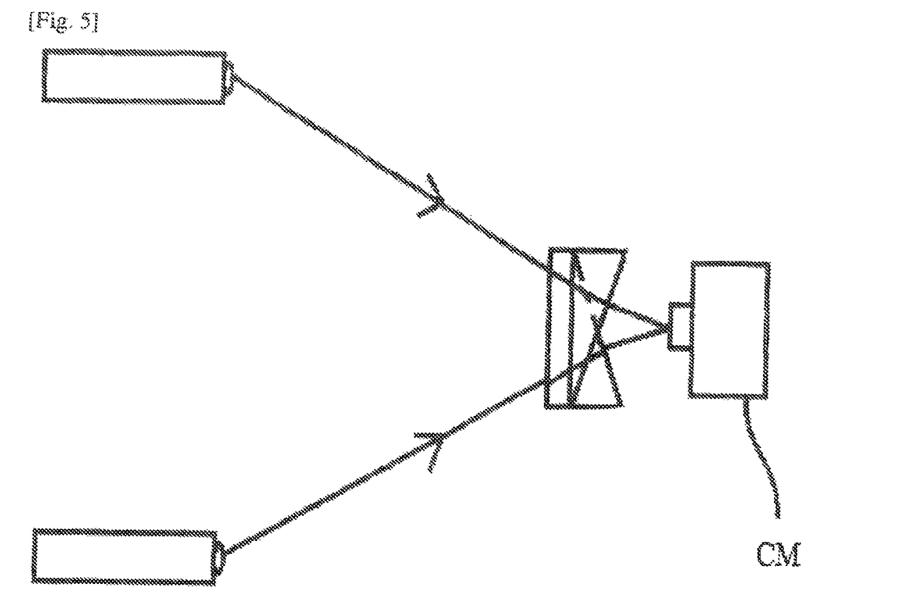
FIG. 5 is a plan view of the row division prism.
Figure 6:
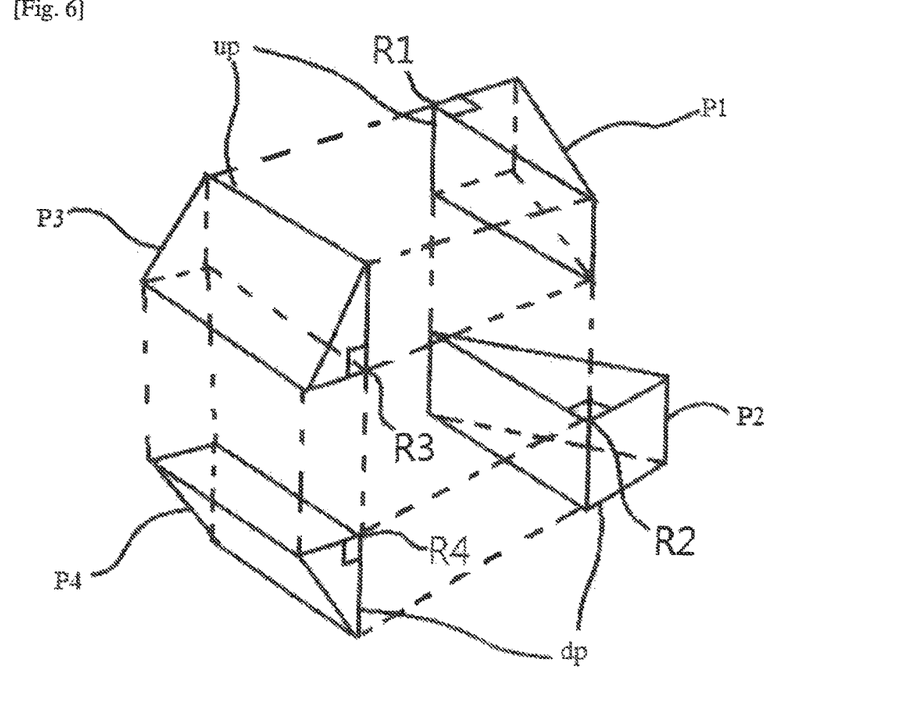
FIG. 6 is an exploded view of the row division prism.

In order to solve this problem, it is preferable to provide a row division prism (PS) of the present invention in front of the camera as shown in FIG. 1. FIG. 3 is a detailed view of a row division prism installed in front of the camera, FIG. 4 is a side view thereof, and FIG. 5 is a top view. FIG. 6 is a view showing a row division prism divided into four simple rectangular prisms. When the row division prism of this embodiment is used, a large number of keys to the far left and the far right can be captured at a time by one camera.

Figure 12:
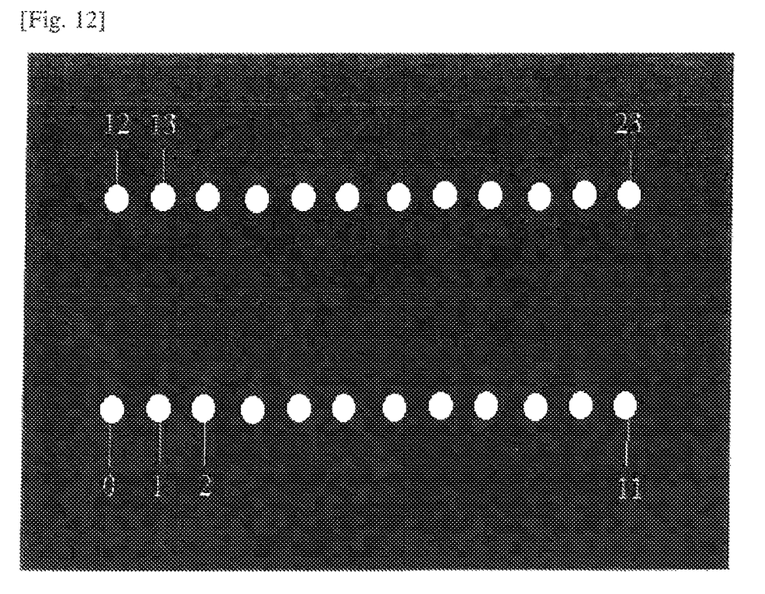
FIG. 12 is an image of marks of a keyboard with row division prism installed in front of a camera.

FIG. 12 is a view of the light retroreflected by the retroreflective films (SR) of keys on a keyboard captured by a camera through a prism as shown in FIG. 3. In FIG. 12, the keys 0 to 11 of the 24 keys are captured in the lower horizontal region of the image, and the remaining 12 to 23 keys are captured in the upper horizontal region of the image. On the other hand, images captured without using the prism contain one horizontal line of bright small spots as shown in FIG. 11. In this way, there is a problem in that each key is captured so small that it is difficult for the image processing means to detect the movement of the key, and that many wasted pixels are not used for capturing keys.

The third (P3, third optical portion) and fourth prisms (P4, fourth optical portion) in FIG. 6 refract light ray such that the far left and far right keys are separately captured in two rows in the camera field of view. That is, the third prism refracts the light reflected slightly upward from the horizontally downward mark (SR), and the fourth prism refracts the light reflected slightly downward from the horizontally upward mark.

The first prism (P1, first optical portion) and the second prism (P2, second optical portion) refract the light rays toward right and left respectively wherein the light rays are refracted and separated as 2 rows by the third and fourth prism. It is preferable that the first and second prisms are formed in the same shape and the third and fourth prisms are formed in the same shape.

A light source (LS) such as an infrared LED may be installed above the first prism and below the second prism, but in this case, it is inconvenient to perform the installation work twice and to manufacture two light source modules. Therefore, it is preferable that the light source module (LS) is formed as one module and is installed between the first and second prisms as shown in FIG. 9.

Figure 8:
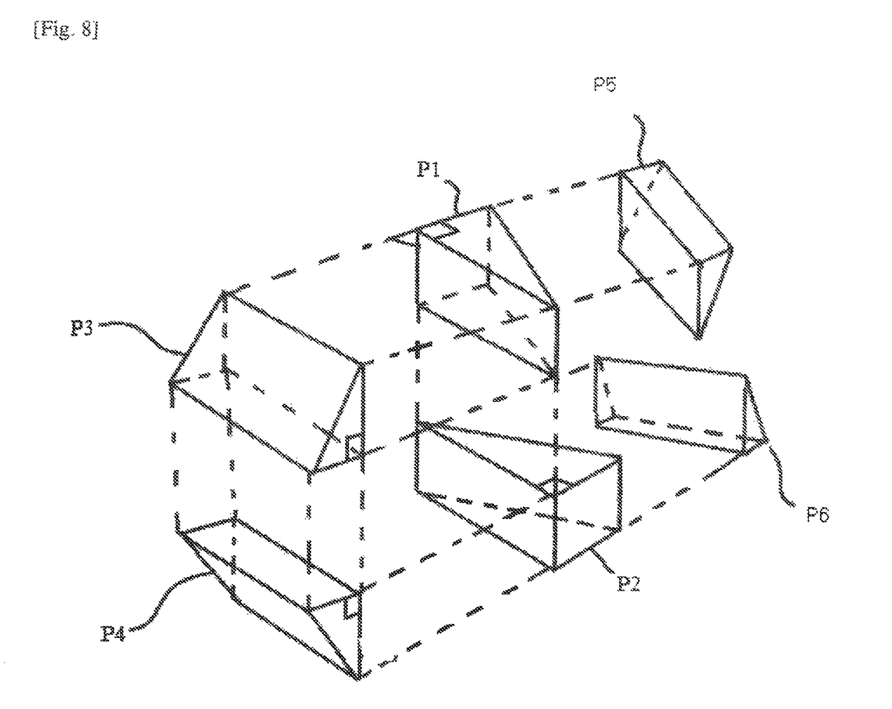
FIG. 8 is an exploded view of the row division prism.

It is preferable to install the fifth (P5, fifth optical portion) and sixth (P6, sixth optical portion) prism between the first and second prisms and the camera lens as shown in FIG. 8 so that the light source module does not obscure the camera field of view (i.e., move the upper field of view of the camera upward and move the lower field of view further down).

The fifth prism may be formed obliquely as shown in FIG. 8 so that the points on the opposing surfaces of the first prism and the fifth prism may be in contact with each other so that the first prism and the fifth prism may be integrally formed. Similarly, the second prism may be formed obliquely as shown in FIG. 8 so that the points on the opposite surfaces of the second prism and the sixth prism may be in contact with each other, so that the second prism and the sixth prism may be integrally formed.

Figure 9:
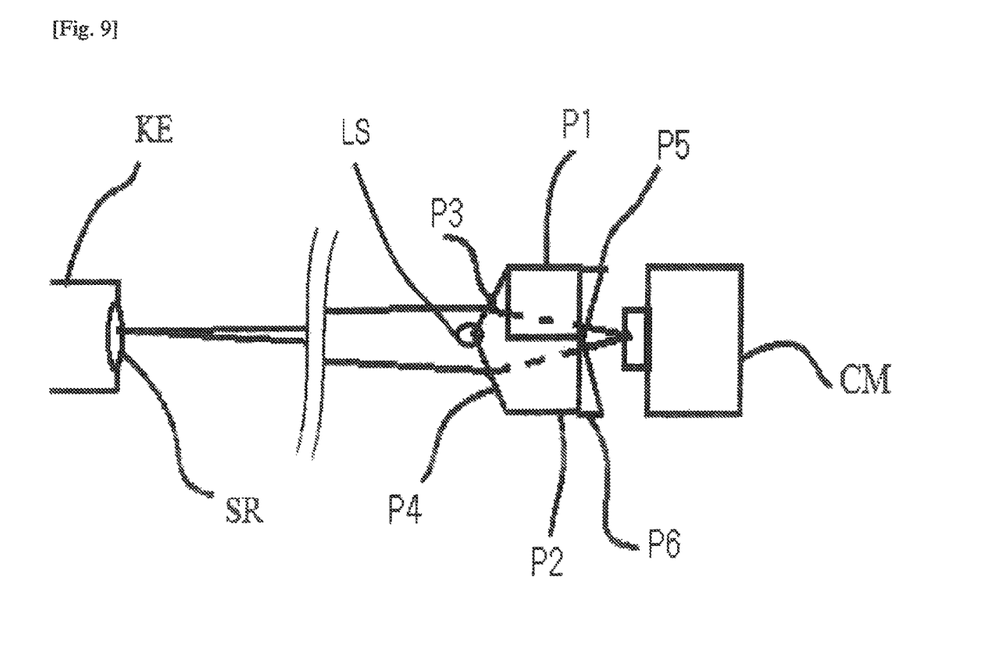
FIG. 9 is a side view of the prism of FIG. 8.

FIG. 9 is a side view of the said prisms.

Figure 7:
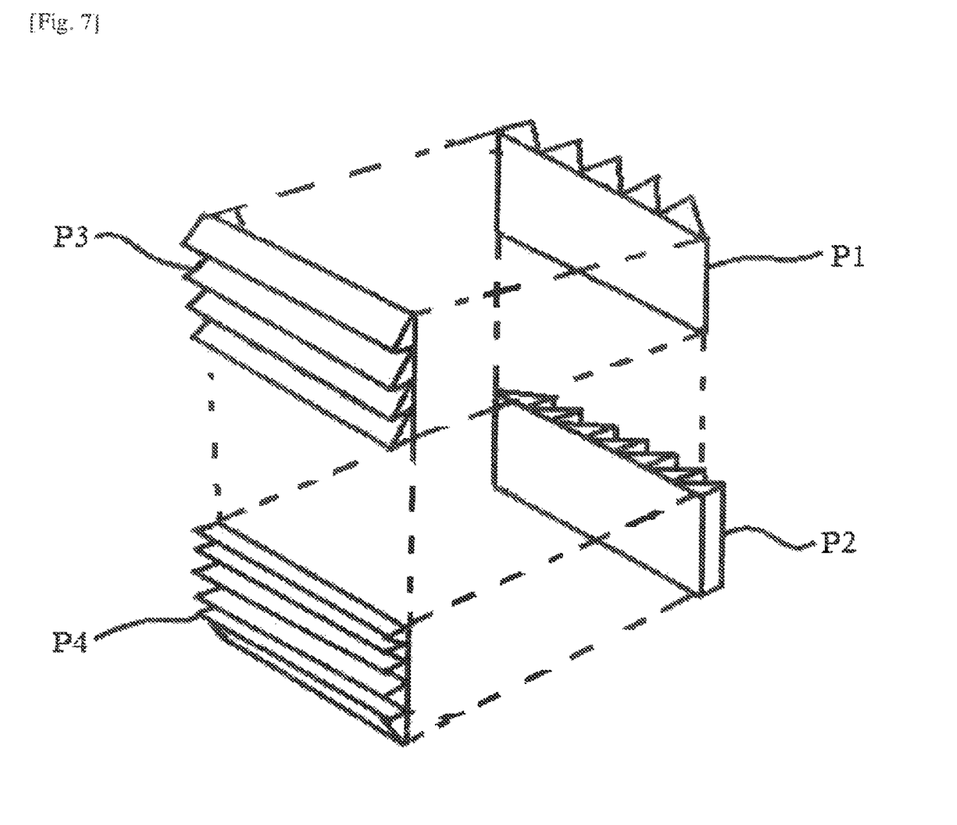
FIG. 7 is an exploded view of the prism sheet.

Such a prism may be formed of a prism sheet of a Fresnel lens type or a hologram as shown in FIG. 7 so as to take up a small volume. That is, such a prism can be implemented with any optical module having a refraction function. As shown in FIG. 6, right-angled portions (R3, R4) of the third and fourth prisms are attached so as to be in contact with each other to form an isosceles triangular prism, and the right angle portions (R1, R2) of the first and second prisms are attached so as to be in opposite direction, so that the row division prism of this embodiment can be formed. The third, fourth, fifth, and sixth prisms may be omitted.

Figure 10:
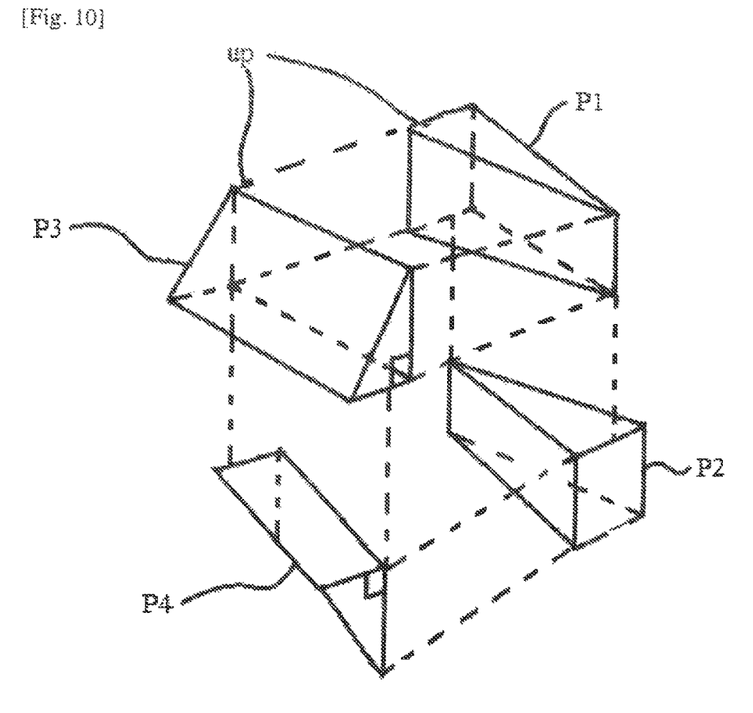
FIG. 10 is a modification of the configuration of FIG. 6.

The first and second prisms shown in FIG. 6 may be formed by a general triangular prism (for example, an isosceles triangle) instead of the right angle prism as shown in FIG. 10. In this case, it is preferable that the third prism is formed obliquely as shown in FIG. 10 so that all points on the opposite surfaces of the first prism and the third prism can contact each other. Similarly, it is preferable that the fourth prism is formed at an angle as shown in FIG. 10 so that all the points on the surface facing the second prism can contact with each other.

In this way, the prism can be formed as an integral prism by forming two prisms opposed to each other in contact with each other and attaching two prisms (for example, acrylic prisms) with an adhesive (for example, acrylic bond).

In FIG. 1, the left and right halves of the keyboard are captured with two cameras (CM1,CM2) respectively. If the number of keys is small, only one camera is sufficient. If there are many keys, then two or more camera can be used. In front of each camera, a prism as shown in FIG. 3 is provided to refract the beams toward camera wherein the beams are coming from the left and right sides of the camera. The left keys are captured in a horizontal line area at the lower (or upper) side of the image and the right keys can be captured in a horizontal line at the upper (or lower) side of the image. That is, the image of the keys towards the left and the right of the keyboard (ROW) is divided into two short lines in the image, and the two lines can be arranged up and down in the camera field of view respectively.

Figure 13:
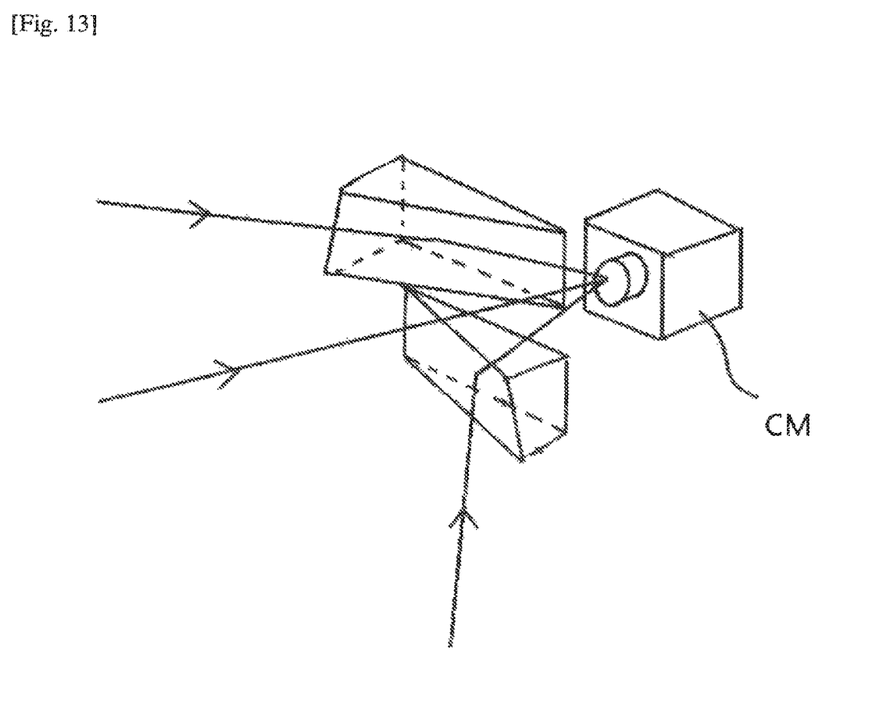
FIG. 13 is a modification of row division prism.
Figure 14:
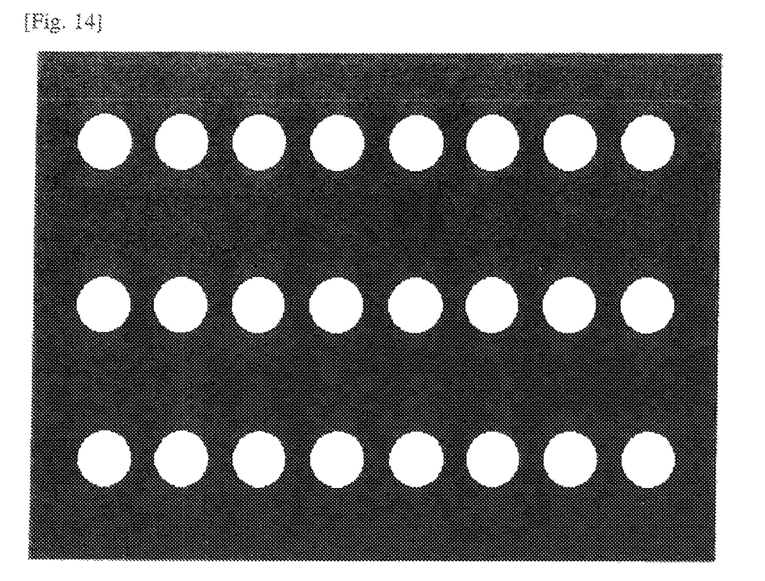
FIG. 14 is an image of marks of a keyboard with the row division prism of FIG. 13 installed in front of a camera.
Figure 15:
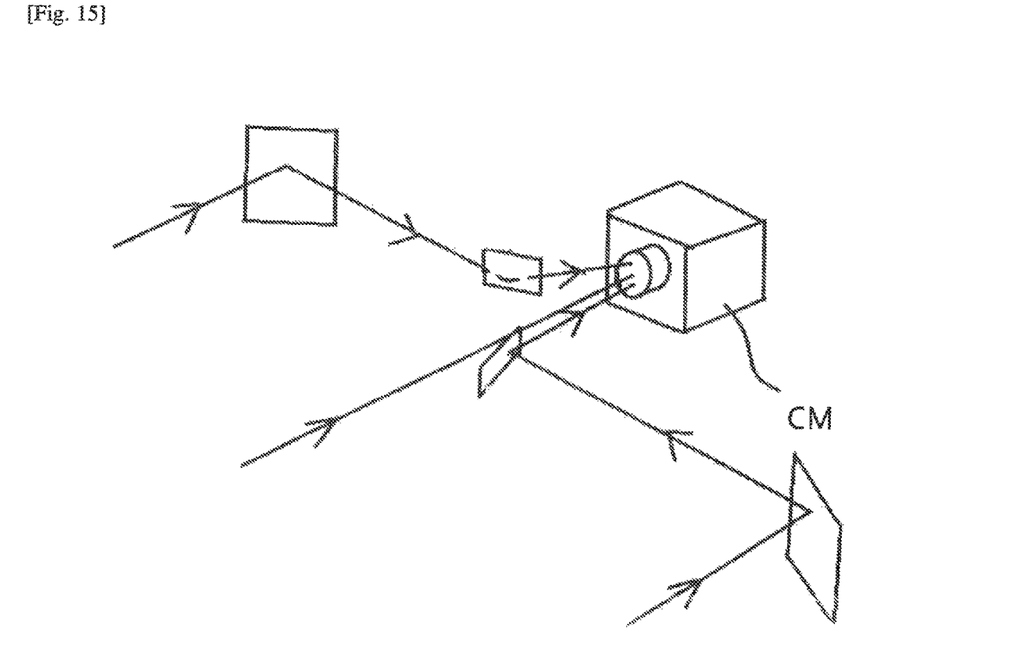
FIG. 15 is a perspective view of a row division optical module using a periscope.

FIG. 13 shows a configuration in which a space is provided between two prisms in front of the camera, and a keyboard is captured through the spaces. The keys are captured with such a configuration in three rows as shown in FIG. 14. FIG. 15 is a configuration for capturing a keyboard in three rows using a periscope-type mirror instead of a prism. An optical module (e.g., prism, hologram, periscope mirror module, etc.) capable of capturing such a long object at a high resolution at one time is referred to as a row division optical module in the present invention.

Retroreflective film is a product sold by 3M Company, which reflects incident light to the light source. By attaching retroreflective films of different colors to two adjacent keys of the keyboard, each key can be distinguished by image processing means for tracking their motion.

For example, a red retroreflective film is attached to a black key, a blue retroreflective film is attached to a white key, a color camera captures it, and an image processing means analyzes the color of the captured image to track the bright portion. By doing this, the motion of keys can be detected more accurately.

A retroreflective film of a different color (e.g., green) or of two colors (red, blue) can be attached to a specific key (for example, the beginning key of the middle octave, i.e., the middle do). By detecting the particular color with the image processing means, the image processing means can easily recognize the order of the surrounding keys. Alternatively, the shape of the retroreflective film may be differently formed to display the reference position of a specific key. For example, a retroreflective film of a normal key may be a polygon such as a square, and a retroreflective film of a keyboard at a reference position may be circular.

Figure 22:
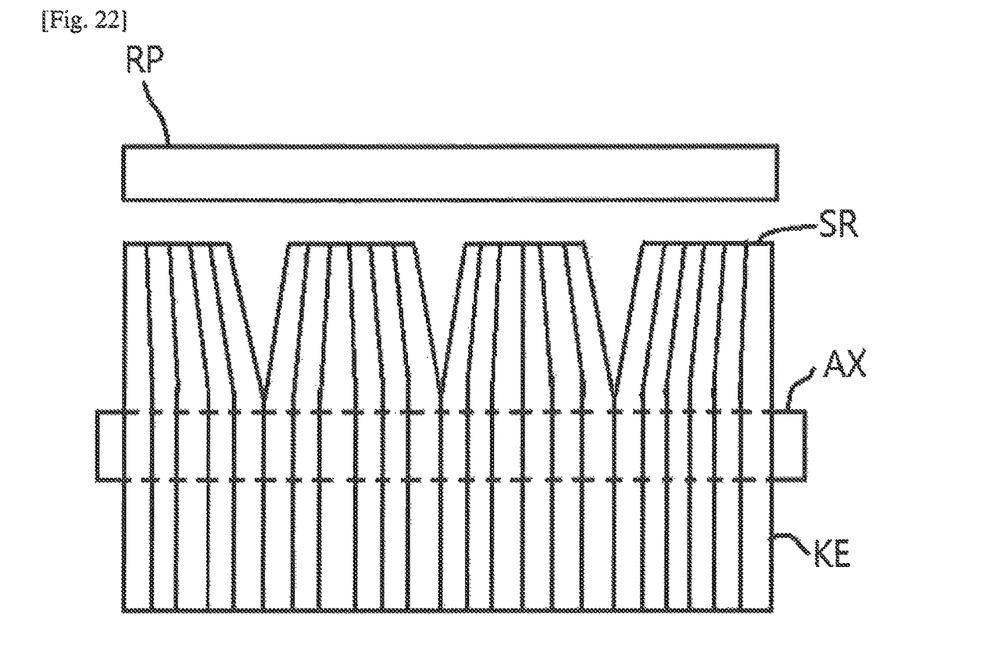
FIG. 22 shows the keyboard in which the interval between marks of the keyboard is adjusted differently.

The interval of the retroreflective film may be adjusted to display the key of the specific reference position. For example, as shown in FIG. 22, the gap between adjacent retroreflective films can be reduced or greatly adjusted.

Since the depth (angle) of the key which is pressed and the moving distance of the retroreflective film or mark in the captured image are approximately proportional, the position of the retroreflective film of each key on the captured image is tracked so that the depth and a sound corresponding to that depth can be an output. For example, a slightly higher frequency can be the output, proportional to the depth of the key press.

In this case, by varying the depth of the pressing, a playing effect can be created wherein the effect is the sound resulting from vibrating the finger pressing a guitar or violin string. It is also possible to increase the size (volume) of the sound in proportion to the depth of depression. It is also possible to detect the force with which the key is pressed and increase the volume of the piano sound in proportion to this force.

Figure 2:
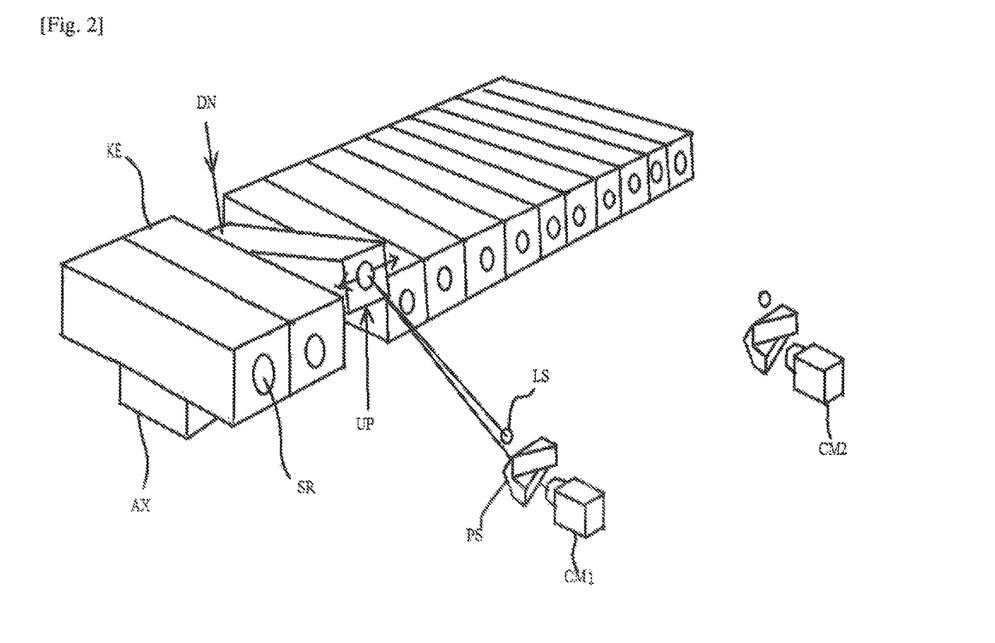
FIG. 2 is a block diagram of an embodiment of the present invention.

Alternatively, as shown in FIG. 2, by capturing the vibration of the keys with cameras to the left and right, and by detecting the vibration by the image processing means, it is possible to implement the function of the modulation wheel, pitch band, or aftertouch. In this case, the retroreflective film attached to the keyboard in the captured image appears to vibrate in a left and right direction. For this purpose, it is preferable to configure the keyboard so as to be movable not only vertically but also horizontally.

That is, the function of the modulation wheel, the pitch band, or the aftertouch of the conventional master keyboard can be implemented by detecting the degree or direction of movement when pressing each key.

In the case of the conventional electronic keyboard, the depth detecting circuit increases in proportion to the number of keys.

However, in the circuit according to the present invention, even if the number of keys is increased, the number of cameras need not be increased in proportion to the number of keys. In addition, since it is a non-contact detection method using a camera instead of using a switch including a physical electric terminal, problems of contact failure, friction, and chattering occurring in the electric terminal are blocked. This function can be used, for example, to obtain the effect of continuously varying the pressing force of a string when playing strings such as a gayageum or a kayagum.

Figure 16:
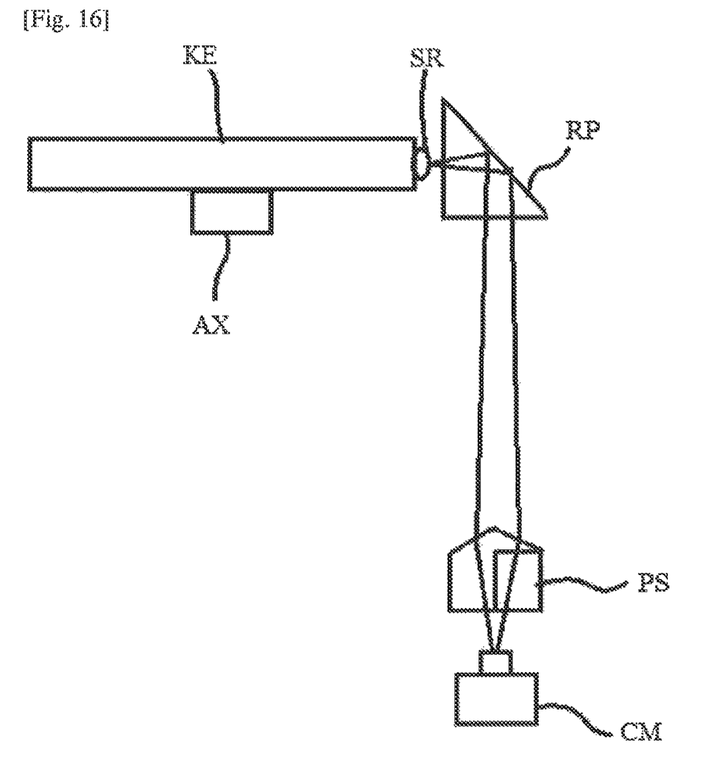
FIG. 16 shows the camera installed on the bottom of the keyboard.
Figure 20:
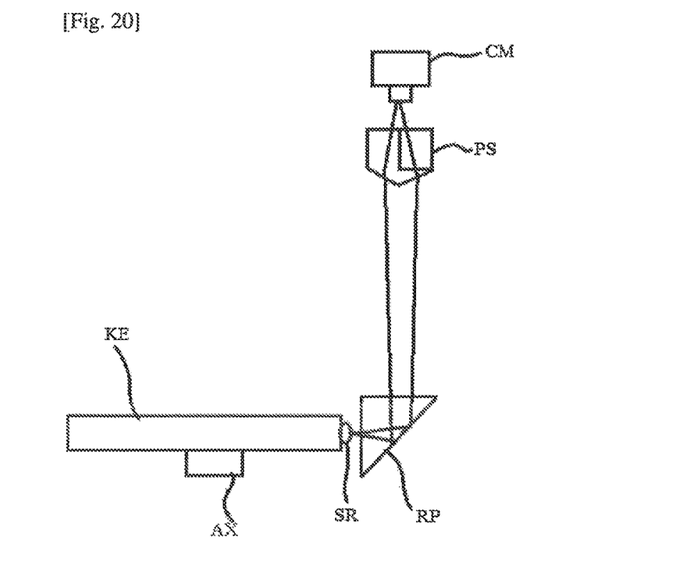
FIG. 20 shows the camera installed over the keyboard.
Figure 21:
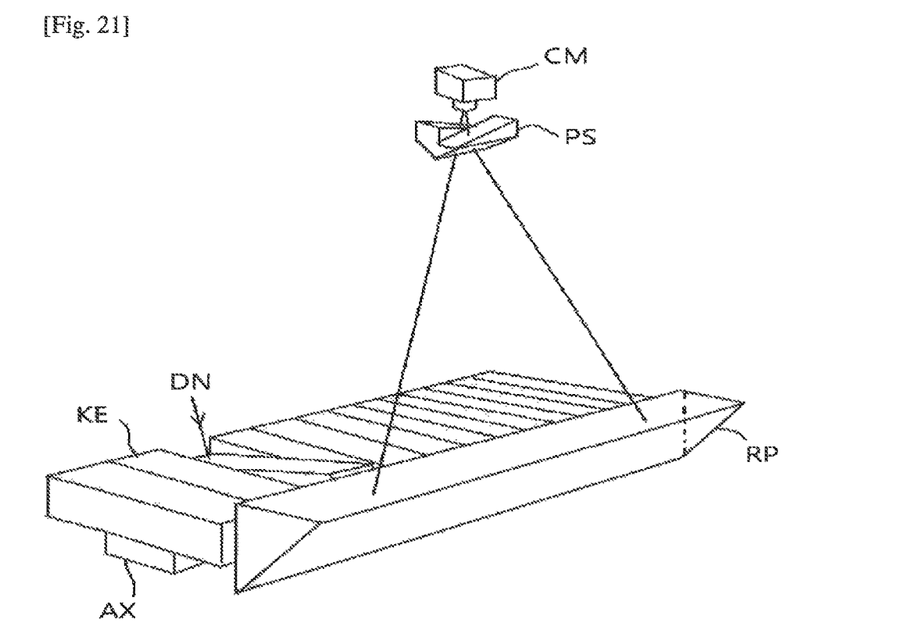
FIG. 21 is a perspective view of FIG. 20.

In order to reduce the volume of the apparatus, a camera may be installed below or above the keyboard as shown in FIG. 16 or 20 by installing a right angle prism (RP) or mirror between the camera and the keyboard. FIG. 21 is a perspective view of FIG. 20.

Figure 17:
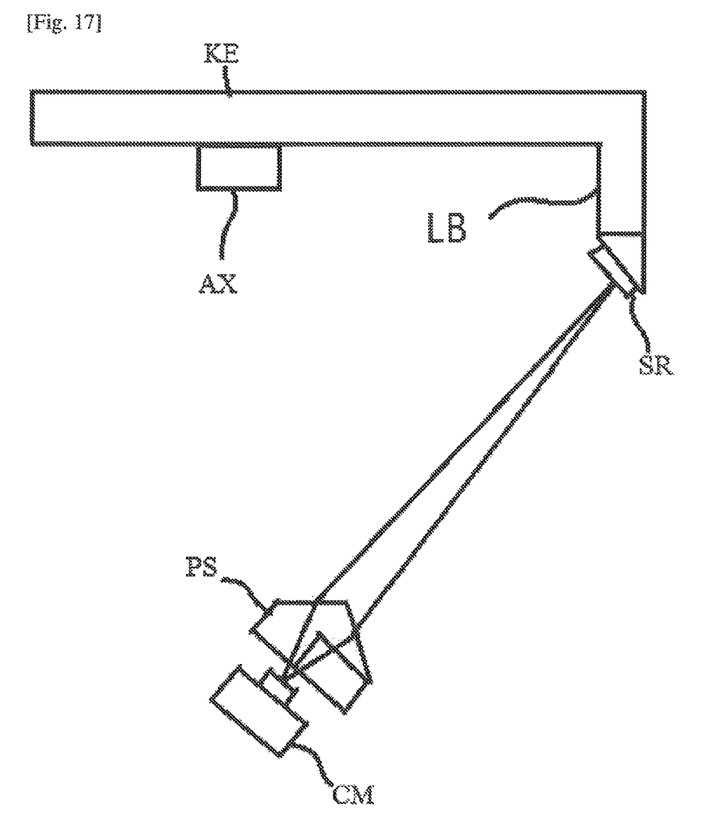
FIG. 17 shows the camera being installed at an angle to the underside of the keyboard.
Figure 18:
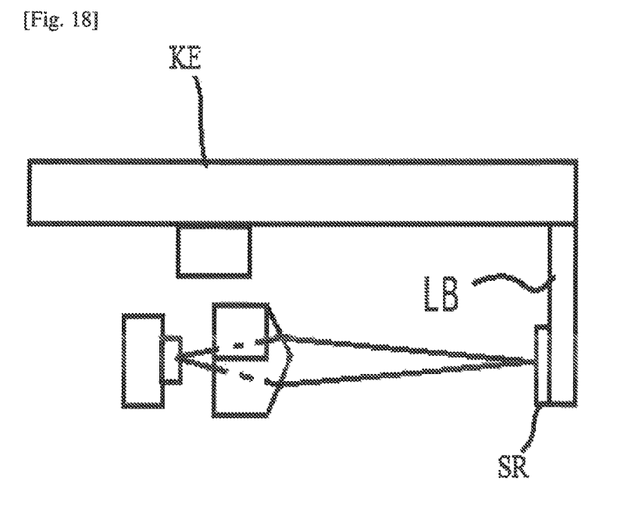
FIG. 18 shows the camera installed just below the keyboard.

Instead of the right angle prism of FIG. 16, the camera is moved further down the keyboard as shown in FIG. 17 or FIG. 18, and a rod (LB) is attached to the end portion of the keyboard in the L shape, and retroreflective film (SR) may be attached. If more than one camera is used (for example, two cameras are used in case of 88 keys), it is recommended that a large number of cameras be installed near the key pedal.

Figure 19:
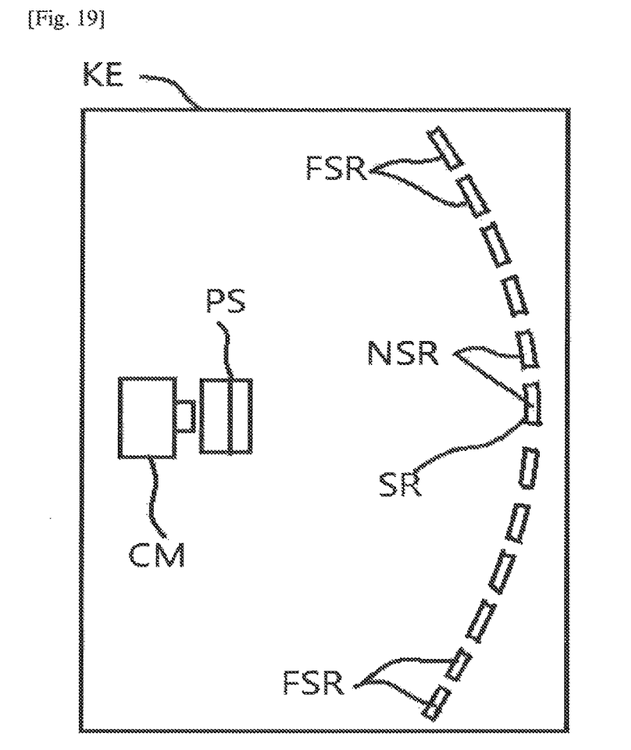
FIG. 19 is a top view of the configuration of FIG. 17 or FIG. 18.

FIG. 19 is a top view of FIG. 17 or FIG. 18. In order to mitigate the distortion of the retroreflective film located at the left and right ends of the camera field of view, it is preferable for the retroreflective films to be placed on a curve (for example, an ellipse having a center on the camera side) as shown in FIG. 19.

Also, it is recommended that the size of the retroreflective film (FSR) on the keys at the far left and right ends from the camera is increased, and the size of the retroreflective film (NSR) on the keys closer to the camera is decreased in order to capture all the retroreflective films at the same size.

It is recommended that the interval between the adjacent retroreflective films (FSR) of the left and right end portions far from the camera increases and the interval between the adjacent retroreflective films (FSR) closer to the camera decreases so that the intervals of all the retroreflective films can be captured at the same size.

Also, when not playing for a long time, it is desirable to reduce the electricity consumption by automatically turning off the light source and the camera. For this purpose, it is preferable to automatically turn off the light source and the camera and to allow for it to fall in the sleep mode when the time for which the motion of the keyboard is not detected in the image processing program exceeds the threshold time.

Here, for example, the sleep mode can be the repeat of turning on the light source and the camera for one second, and turning off the light source and the camera for two seconds, wherein the capturing occurs during the turning on period. If the movement of the keyboard is detected during this sleep mode, the original normal mode (mode in which the light source and camera are always turned on) can be restored.

The invention claimed is:
1. An image capturing device comprising:
a camera for capturing images;
a first optical portion for changing direction of light incident on the first optical portion from a right side of the camera, toward the camera, wherein an image to be captured by the camera extends along a first direction and has a right side and a left side along the first direction; and a second optical portion for changing direction of light incident on the second optical portion from a left side of the camera, toward the camera, wherein the first and second optical portions are arranged along a second direction, transverse to the first direction, with the first optical portion spaced apart from the second optical portion by a space through which light that is captured by the camera passes, the camera captures respective first, second, and third images of the light incident on the first optical portion, passing through the space between the first and second optical portions, and incident on the second optical portion, and the first, second, and third images are separated from each other and appear along three respective rows.

2. The image capturing device of claim 1, wherein each of the first and second optical portions comprises one of a prism, a prism sheet, a hologram, and a mirror.

3. An electronic keyboard device comprising:

a keyboard including a plurality of individually movable keys arranged along a first direction, wherein the keyboard has right and left sides along the first direction;

an image capturing device comprising
a camera for capturing images,
a first optical portion for changing direction of light incident on the first optical portion from a right side of the keyboard, toward the camera, and
a second optical portion for changing direction of light incident on the second optical portion from the left side of the keyboard, toward the camera, wherein
the first and second optical portions are arranged along a second direction, transverse to the first direction, with the first optical portion spaced apart from the second optical portion by a space through which light that is captured by the camera,
the camera captures respective first, second, and third images of the keys from the light incident on the first optical portion, passing through the space between the first and second optical portions, and incident on the second optical portion, and
the first, second, and third images are separated from each other and appear along three respective rows; and image processing means for detecting movement of respective keys from the first, second, and third images captured by the camera, and outputting a musical instrument sound or a musical instrument digital interface (MIDI) signal corresponding to each movement of a key that is detected.

4. The electronic keyboard device of claim 3, wherein each of the first and second optical portions includes one of a prism, a prism sheet, a hologram, and a mirror.

5. The electronic keyboard device of claim 3, wherein each of the keys includes a mark, and
the image processing means detects the marks in the images captured to identify the movement of respective keys.

6. The electronic keyboard device of claim 5, wherein the marks are retroreflecting means.

7. The electronic keyboard device of claim 3, wherein
the keyboard has an L shaped bar attached to the keyboard, beneath the keyboard,
the camera is located beneath the keyboard and captures an image of the bar, and
the image processing means detects motion of the bar on the image captured and outputs the musical instrument sound or the MIDI signal.

8. The electronic keyboard device of claim 3, wherein
the keyboard includes a right angle prism or a mirror, and
the camera captures images for detecting the movement of the keys via the right angle prism or the mirror and is positioned below or above the keyboard.

9. The electronic keyboard device of claim 3, wherein the image processing means outputs a musical instrument sound or a MIDI signal in proportion to speed of movement of a key or depressed depth of a key.

\* \* \* \* \*